United States Patent [19]
Lo et al.

[11] Patent Number: 5,514,641
[45] Date of Patent: May 7, 1996

[54] SOLID HERBICIDAL COMPOSITIONS CONTANING N-PHOSPHONOMETHYLGLYCINE

[75] Inventors: Ray J. R. Lo, San Leandro; Candice W. Huang, Lafayette, both of Calif.

[73] Assignee: Zeneca Limited, London, England

[21] Appl. No.: 334,509

[22] Filed: Nov. 4, 1994

[51] Int. Cl.$^6$ .................................................. A01N 37/12
[52] U.S. Cl. ........................................... 504/206; 504/116
[58] Field of Search ...................................... 504/206, 116

[56] References Cited

U.S. PATENT DOCUMENTS 5,362,705  11/1994  Moucharafieh et al. ................ 504/206

*Primary Examiner*—Allen J. Robinson
*Assistant Examiner*—Brian G. Bembenick
*Attorney, Agent, or Firm*—Joel G. Ackerman

[57] ABSTRACT

Solid herbicidal compositions contain N-phosphonomethylglycine and an alkyl phenol polyoxyethylene surfactant containing from about 50 to about 90 weight percent of an alkyl phenol polyoxyethylene carboxylic acid.

8 Claims, No Drawings

SOLID HERBICIDAL COMPOSITIONS CONTANING N-PHOSPHONOMETHYLGLYCINE

BACKGROUND OF THE INVENTION

This invention relates to novel solid herbicidal compositions containing the herbicide N-phosphonomethylglycine (also known as glyphosate) together with a solid alkyl phenol polyoxyalkylene carboxylic acid-containing surfactant.

N-phosphonomethylglycine, as well as analogous compounds including salts, and the herbicidal properties and formulations containing them, are described in numerous patents such as U.S. Pat. No. 3,799,758. This patent describes a number of compositions containing N-phosphonomethylglycine and analogous compounds and discloses that the incorporation of a surface-active agent into such compositions "greatly enhances their efficiency".

That patent generally discloses that solid compositions of various types may be prepared, but no specific examples of solid compositions are mentioned.

Solid compositions containing N-phosphonomethylglycine, however, are mentioned in a number of references including European Patent Applications Nos. 448538 and 498145 and U.S. Pat. Nos. 4,931,080 and 5,118,338.

Copending U.S. application Ser. No. 08/90,583 (U.S. Pat. No. 5,362,705) Nadim Moucharafieh et al. discloses the preparation of dilute aqueous compositions containing from about 0.1 to about 1.5 weight percent N-phosphonomethylglycine and from about 0.1 to about 5 weight percent of an alkyl phenol polyoxyalkylene surfactant containing from about 50 to about 90 weight percent alkyl phenol polyoxyethylene carboxylic acid. The patent application mentions that one means of forming such compositions is to first prepare a concentrate containing N-phosphonomethyl-glycine or one of its more water-soluble derivatives (such as an alkali metal or amine salt) with the alkyl phenol polyoxyalkylene surfactant and then dissolving the concentrate in water. This information represents the work of the present inventor, which is disclosed in more detail and claimed herein.

SUMMARY OF THE INVENTION

This invention comprises a solid herbicidal composition comprising (a) from about 30 to about 60 percent by weight N-phosphonomethylglycine; and (b) from about 20 to about 50 percent by weight of a solid alkyl phenol polyoxyethylene surfactant containing from about 50 to about 90 weight percent of an alkyl phenol polyoxyethylene carboxylic acid.

DETAILED DESCRIPTION OF THE INVENTION

The compositions of this invention are prepared by conventional blending and mixing techniques, plus extrusion, air drying, spray drying, granulation, etc. according to the desired final form of the product. In general, technical grade N-phosphonomethylglycine is mixed with the alkyl phenol polyoxyalkylene carboxylic acid surfactant, and optionally one or more other surfactants. For better mixing, the alkyl phenol polyoxyalkylene carboxylic acid-containing surfactant may be melted, either by heating it prior to mixing it into the composition, or by heating the composition after the surfactant has been added. Alternatively, the surfactant and/ or other ingredients may be mixed with water, in order to provide better mixing for the overall composition, with the water subsequently being removed by air drying, spray drying, or other conventional technique.

In addition to the alkyl phenol polyoxyalkylene carboxylic acid-containing surfactant, compositions of this invention may also contain additional surfactants such as alkyl polyglycosides, poly(hydroxyalkyl)amines, ethoxylated fatty alcohols and high molecular weight (methoxy)polyethylene glycols. Examples of alkyl polyglycosides include AL-2042 and Atplus 258, obtainable from Imperial Chemical Industries PLC and the Agrimul series obtainable from Henkel Corporation. Examples of poly(hydroxyalkyl) substituted amines include tris(hydroxymethyl)amino methane ("Tris"), N-tris(hydroxymethyl)methyl glycine("Tricine"), and N,N-bis(2-hydroxyethyl)glycine ("Bicine"). Examples of ethoxylated fatty alcohols include Berol 08 P, available from Berol Nobel AB. Examples of high molecular weight (methoxy) polyethylene glycols include Carbowax MPEG-5000, available from Union Carbide.

The surfactants which have been found useful in compositions according to this invention contain from about 50 to about 90 weight percent of an alkyl phenol polyoxyethylene carboxylic acid, namely a compound having the formula

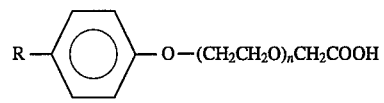

in which R is a $C_8$–$C_{20}$ alkyl group, most preferably a $C_8$–$C_9$ alkyl group, and n is a value of from about 50 to about 150, preferably about 100. In general, the surfactant overall is a nonionic alkyl phenol polyoxyethylene surfactant in which a major portion of the composition has been converted from the corresponding nonionic alcohol or ether to the weak electrolyte anionic carboxylic acid. One example of such a surfactant is Sandopan MA-200 (R=nonyl, n=100), available from Sandoz.

The following represent examples of preparation of compositions according to this invention.

EXAMPLE 1

A composition was prepared having the following ingredients

|  | Wt. % | Wt., g |
| --- | --- | --- |
| N-phosphonomethylglycine (96.1% purity) | 58.8 | 29.4 |
| Tris | 11.8 | 5.9 |
| Sandopan MA-200 | 29.4 | 14.7 |

The ingredients were mixed in a grinder and the mixture, which was lumpy, was air dried.

EXAMPLE 2

A composition was formed as follows:

|  | Wt. % | Wt., g |
| --- | --- | --- |
| N-phosphonomethylglycine (97.2% purity) | 50.0 | 25.0 |
| AL-2042 Surfactant (contains 30% by weight water) | 25.0 | 25.5 |
| Sandopan MA-200 | 25.0 | 12.5 |

The AL-2042 was warmed up in one flask and a second flask containing the Sandopan MA-200 was heated to melt that surfactant. The two surfactants were mixed together, then the N-phosphonomethylglycine was added and the three components were further mixed. A paste was formed which was air dried.

EXAMPLE 3

A composition was formed containing the following ingredients:

|  | Wt. % | Wt., g |
|---|---|---|
| N-phosphonomethylglycine (97.2% purity) | 45.4 | 22.7 |
| AL-2042 | 22.8 | 11.4 |
| Sandopan MA-200 | 22.8 | 11.4 |
| Tris | 9.0 | 4.5 |

The AL-2042 and Sandopan were warmed and melted, respectively, and mixed together, as in EXAMPLE 2. Then the tris was added, followed by the N-phosphonomethylglycine and further mixing. The product was a paste which was air dried.

EXAMPLE 4

A composition was formed having the following ingredients:

|  | Wt. % | wt., q |
|---|---|---|
| N-phosphonomethylglycine (97% purity) | 50.0 | 40.0 |
| Agrimul PG-2067 (contains 30% by weight water) | 25.0 | 14.0 |
| Sandopan MA-200 | 25.0 | 20.0 |

The Sandopan was dissolved in 250 ml water, then the Agrimul PG-2067 was dissolved in that solution. Next the N-phosphonomethylglycine was added. The composition was then mixed and spray dried.

EXAMPLE 5

A composition was prepared having the following ingredients (after drying):

|  | Wt. % | Wt., g |
|---|---|---|
| N-phosphonomethylglycine (97% purity) | 50.0 | 50.5 |
| AL-2042 | 25.0 | 25.0 |
| Sandopan MA-200 | 25.0 | 25.0 |

The ingredients were mixed together, then 250 ml water was added. The overall mixture was heated at 45° C. to melt the Sandopan. The resulting mixture was passed through a 50 mesh screen, then spray dried.

EXAMPLE 6

A composition was formed having the following ingredients:

|  | Wt. % | Wt., g |
|---|---|---|
| N-phosphonomethylglycine (97% purity) | 50.0 | 15.0 |
| Sandopan MA-200 | 25.0 | 7.5 |
| Berol 08 P | 25.0 | 7.5 |

The ingredients were mixed with the addition of approximately 1.5 ml water to improve the mixing.

EXAMPLE 7

A composition was formed having the following ingredients:

|  | Wt. % | Wt., g |
|---|---|---|
| N-phosphonomethylglycine (97% purity) | 50.0 | 15.0 |
| Sandopan MA-200 | 50.0 | 15.0 |

The ingredients were mixed with the addition of approximately 1.5 ml water to improve the mixing.

EXAMPLE 8

A composition was formed having the following ingredients:

|  | Wt. % | Wt., g |
|---|---|---|
| N-phosphonomethylglycine (97% purity) | 66.7 | 15.0 |
| Sandopan MA-200 | 33.3 | 7.5 |

The ingredients were mixed in a grinder with approximately 1.5 ml water being added for better mixing.

EXAMPLE 9

A composition was prepared having the following ingredients:

|  | Wt. % | Wt., g |
|---|---|---|
| N-phosphonomethylglycine (97% purity) | 33.4 | 15.0 |
| Sandopan MA-200 | 33.3 | 15.0 |
| Carbowax MPEG-5000 | 33.3 | 15.0 |

The ingredients were mixed in a grinder, then approximately 1.5 ml water was added and the ingredients mixed together. The product was placed in an evaporating dish for removal of water.

EXAMPLE 10

A composition was prepared having the following ingredients:

|  | Wt. % | Wt., g. |
|---|---|---|
| N-phosphonomethylglycine | 43.2 | 60.0 |

|  | Wt. % | Wt., g. |
|---|---|---|
| (97.9% purity) | | |
| Sandopan MA-200 | 21.6 | 30.0 |
| AL-2042 | 21.6 | 30.0 |
| Sipernat 50 Silica | 13.6 | 19.0 |

N-phosphonomethylglycine and Sandopan MA-200 were mixed well. Then, while mixing the composition, there were added in succession 5 grams silica, 15 grams AL-2042, a further 5 grams silica, the remaining 15 grams AL-2042 and the remainder of the silica, until the mixture was moist enough to be extruded. The extrudates were allowed to air dry and then dried at 50° C. in an oven.

BIOLOGICAL EVALUATION

The compositions described in the foregoing examples were evaluated for herbicidal activity as follows:

The following weeds were used in the tests: *Lolium perenne* (perennial ryegrass, LOLPE), *Abutilon theophrasti* (velvetleaf, ABUTH), and *Ipomoea hedera* (ivyleaf morningglory, IPOHE).

The compositions were applied post-emergence at application rates of 0.125, 0.250, 0.500 and 1.00 lb/acre based on N-phosphonomethylglycine content, using three replications. The spray volume was 25 gallons per acre (234 l/ha); plants were treated 20–24 days after the plants had been seeded. Ratings were taken at 10–15 and 20–24 days after application, with the plants being visually rated on a scale of from 0 to 100 in which 0 represented no effect as compared to an untreated control flat, and 100 represented complete kill.

Table I shows results of testing EXAMPLEs 1 through 10 with desiccation evaluated at 10–15 days after treatment. The results are averages taken over all four application rates. Table II shows control of weeds in the test evaluated at 20–24 days after treatment, again as averages over all four rates of application.

TABLE I

| | % Desiccation, 10–15 DAT | | |
|---|---|---|---|
| EXAMPLE | LOLPE | ABUTH | IPOHE |
| 1 | 56.9 | 51.7 | 37.5 |
| 2 | 66.9 | 57.3 | 37.5 |
| 3 | 67.3 | 53.6 | 38.3 |
| 4 | 49.2 | 49.6 | 34.2 |
| 5 | 71.3 | 59.2 | 45.8 |
| 6 | 66.5 | 62.3 | 51.3 |
| 7* | 73.2 | 77.6 | 50.0 |
| 8** | 84.7 | 71.3 | 47.1 |
| 9 | 61.3 | 66.3 | 45.0 |
| 10 | 71.8 | 64.2 | 42.5 |

*2.0 wt. % glycerol added
**0.5 wt. % Atplus 258 added

TABLE 2

| | % Control, 20–24 DAT | | |
|---|---|---|---|
| EXAMPLE | LOLPE | ABUTH | IPOHE |
| 1 | 62.8 | 53.8 | 48.6 |
| 2 | 71.7 | 61.3 | 57.2 |
| 3 | 69.8 | 59.2 | 52.3 |
| 4 | 64.8 | 52.3 | 54.2 |
| 5 | 73.8 | 61.7 | 54.4 |
| 6 | 63.8 | 63.2 | 60.8 |
| 7* | 78.3 | 78.2 | 62.5 |
| 8** | 88.2 | 70.9 | 57.9 |
| 9 | 63.6 | 69.0 | 58.6 |
| 10 | 75.0 | 64.8 | 47.5 |

*2.0 wt. % glycerol added
**0.5 wt. % Atplus 258 added

What is claimed:

1. A solid herbicidal composition comprising (a) from about 30 to about 60 weight percent N-phosphonomethylglycine, and (b) from about 20 to about 50 weight percent of an alkyl phenol polyoxyethylene surfactant containing from about 50 to about 90 eight percent alkyl phenol polyoxyethylene carboxylic acid.

2. A composition according to claim 1 in which the alkyl phenol polyoxyethylene carboxylic acid has the formula

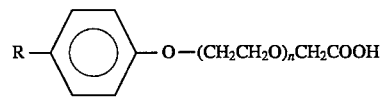

in which R is a $C_8$–$C_{20}$ alkyl group and n is an integer from about 50 to about 150.

3. A composition according to claim 2 in which n is about 100.

4. A composition according to claim 1 further comprising an alkyl polyglycoside surface active agent.

5. A composition according to claim 1 further comprising a poly-(hydroxyalkyl)amine.

6. A composition according to claim 5 in which the poly-(hydroxyalkyl)amine is tris (hydroxymethyl)aminomethane.

7. A composition according to claim 1 in which the weight ratio of N-phosphonomethylglycine to alkyl phenol polyoxyethylene surfactant is about 1:1.

8. A composition according to claim 1 in which the weight ratio of N-phosphonomethylglycine to alkyl phenol polyoxyethylene surfactant is about 2:1.

* * * * *